United States Patent [19]
Fujiso et al.

[11] 4,447,553
[45] May 8, 1984

[54] PROCESS FOR RE-ACTIVATION OF SOLID ACID CATALYST

[75] Inventors: Tokuo Fujiso, Yokosuka; Tadashi Ohmori, Yokohama; Soichi Nomura, Tokyo, all of Japan

[73] Assignee: Nippon Oil Co., Ltd., Tokyo, Japan

[21] Appl. No.: 402,619

[22] Filed: Jul. 28, 1982

[30] Foreign Application Priority Data

Aug. 4, 1981 [JP] Japan ............... 56-122280

[51] Int. Cl.$^3$ ............... B01J 37/12
[52] U.S. Cl. ............... 502/36; 502/35
[58] Field of Search ............... 252/415; 502/35, 36, 502/37

[56] References Cited

U.S. PATENT DOCUMENTS

| | | | |
|---|---|---|---|
| 3,243,384 | 3/1966 | Raarup, Jr. ............... | 252/415 |
| 3,637,524 | 1/1972 | Johnson et al. ............... | 252/415 |
| 3,654,142 | 4/1972 | Moravec, Jr. et al. ............... | 252/415 |
| 3,781,219 | 12/1973 | Johnson et al. ............... | 252/415 |
| 3,939,061 | 2/1976 | Paynter et al. ............... | 252/415 |
| 3,981,824 | 9/1976 | Greenwood et al. ............... | 252/415 |
| 4,083,800 | 4/1978 | Herbstman et al. ............... | 252/415 |

*Primary Examiner*—Delbert E. Gantz
*Assistant Examiner*—Cynthia A. Prezlock
*Attorney, Agent, or Firm*—Bucknam and Archer

[57] ABSTRACT

A process is disclosed for re-activating a used solid acid catalyst wherein the catalyst is calcined to burn off heavy hydrocarbons and subsequently halogenated with chlorine and/or fluorine or their compounds entrained by an inert gas or a non-reducing gas. The resulting re-activated catalyst finds wide application in isomerization and oligomerization of olefins, conversion of methanol into hydrocarbons, and isomerization, disproportionation or trans-alkylation of aromatic hydrocarbons.

3 Claims, No Drawings

PROCESS FOR RE-ACTIVATION OF SOLID ACID CATALYST

BACKGROUND OF THE INVENTION

1. Field of the Invention

This invention relates to a solid acid catalyst, more particularly to such a catalyst comprising active alumina and halogen supported thereon. The invention is still more particularly directed to a process for the re-activation of solid acid catalysts wherein the catalyst composition is thermally treated with an inert gas containing molecular oxygen ($O_2$) and subjected to halogenation with a halogen compound entrained by an inert gas or a non-reducing gas.

2. Prior Art

The present inventors have previously disclosed in Japanese Laid-Open Patent Publication No. 56-28646 certain catalysts suitable for isomerizing aliphatic olefins having a relatively small amount of a branched structure to aliphatic olefins having a relatively large amount of a branched structure. This catalyst comprises an active alumina carrier and fluorine and chlorine supported thereon, the amounts of fluorine and chlorine being 0.3 to 1.0%, and 0.6 to 2.0%, respectively, based on the total weight of the catalyst composition.

SUMMARY OF THE INVENTION

Continued extensive research of the aforesaid catalyst has not indicated that the catalyst is highly useful in not only isomerization but also in oligomerization of olefins, conversion of methanol into hydrocarbons, isomerization, disproportionation or trans-alkylation of aromatic hydrocarbons. The catalyst under contemplation as compared to conventional catalysts is higher in activity and longer in service life, but is not quite satisfactory in that its activity declines over prolonged use due to accumulation of high molecular weight hydrocarbons on the catalyst, or due to isolation of halogen from the catalyst.

It is therefore an object of the present invention to provide a process for re-activating solid acid catalysts that have declined in activity. The process according to the invention is characterized in the re-activation of a solid acid catalyst comprising an active alumina carrier and fluorine and chlorine both supported thereon, the amounts of said fluorine and said chlorine being 0.3-1.0% and 0.6-2.0%, respectively, based on the total weight of the catalyst composition, the process of re-activation which comprises: subjecting the catalyst to a calcination treatment at 350°-550° C. in which it is brought into contact with an inert gas containing molecular oxygen thereby to burn off high molecular weight hydrocarbon that have been deposited on the catalyst during reaction; measuring the contents of fluorine and chlorine in the calcined catalyst to see if the content of fluorine is greater or smaller than 70% of a fresh catalyst; subjecting the calcined catalyst to a halogenation treatment at 200°-500° C. in which it is brought into contact with an inert gas or a non-reducing gas containing 50-1,000 ppm of moisture and entrained with chlorine, its compound or a mixture thereof, in the event the catalyst upon said calcination treatment contains fluorine in an amount greater than 70% of a fresh catalyst; and alternatively, subjecting the calcined catalyst to a halogenation treatment in which it is brought into contact with an inert gas or a non-reducing gas containing 50-1,000 ppm of moisture and entrained with a mixture of chlorine and fluorine, chlorine and a fluorine compound, a chlorine compound and fluorine, a chlorine compound and a fluorine compound, or a compound containing in the molecule both chlorine and fluorine, in the event the catalyst upon said calcination treatment contains fluorine in an amount less than 70% of a fresh catalyst.

DESCRIPTION OF THE PREFERRED EMBODIMENTS

High molecular weight hydrocarbons in the used catalyst are burned to vanish by contacting the catalyst with air or oxygen entrained with an inert gas, in which instance the amount and concentration of oxygen is controlled so that the catalyst temperature is held in the range of 350°-550° C., preferably 350°-500° C. This controlled burning or calcination is initiated by an inert gas such as nitrogen or carbonic gas containing less than 1 mol % of oxygen which should be sufficient to remove a majority of high molecular weight hydrocarbons from the catalyst. To ensure complete removal of the undesirable hydrocarbons, oxygen concentrations may be somewhat increased but with a caution not to exceed the above specified catalyst temperature. Termination of this operation can be determined by measuring the concentration of the carbonic gas in the outlet gas stream which is normally a few times greater than the concentration of inlet gas. The catalyst bed temperature is then reduced about 20°-50° C. lower than the subsequent halogenation temperature of 200°-500° C., followed by changing the circulating gas stream with a non-reducing gas such as nitrogen, air or a mixture thereof that contains 50-1,000 ppm, preferably 100-500 ppm of moisture. The halogenation treatment is effected with due consideration of the contents of fluorine and chlorine in the catalyst after the calcination operation. Halogen is normally eliminated during the course of reaction and calcination. Since active alumina can be more strongly bonded to fluorine than to chlorine, the amount of isolation of fluorine from the catalyst is smaller than that of chlorine. It is therefore necessary to replenish chlorine each time the catalyst is re-activated. Whereas, fluorine may be replenished only when its content in the catalyst has decreased to an extent insufficient to maintain the desired level of activity of the catalyst. Accordingly, the halogenation involves two different cases; namely, either to replenish chlorine alone or to replenish both fluorine and chlorine. Replenishment of fluorine and chlorine should be effected when the content of fluorine after calcination of the used catalyst has decreased to a value less than 70% of a fresh catalyst. With this fluorine content greater than 70% of the fresh catalyst, then chlorine alone should be replenished.

A suitable method of chlorination is to pass a gaseous stream of chlorine or a chlorine compound alone or diluted with an inert gas such as nitrogen or a non-reducing gas such as air, over the active alumina to be treated. The principal factors of this treatment are the temperature and time length which affect the amount of chlorine to be deposited. The amount of chlorine to be supported is also affected by the type, amount, physical properties and shape of the active alumina used, and further by the type and flow rate of chlorine or its compound as well as by the type and amount of the diluent. The suitable chlorination temperature is 200° to 500° C., preferably 350° to 450° C. The length of time for chlorination may be accurately determined by the amount of chlorine to be deposited on a carrier, but it is usually a few minutes to a few hours. The amount of air or nitrogen used for dilution of chlorine is not critical but may be about 10-1,000 times that of chlorine or chlorine compound. This dilution is effective for controlling the temperature of the chlorination treatment. In order to perform the chlorination treatment under mild reaction conditions and thus to deposit chlorine more uniformly, water may be present in an amount of 5-1,000 mole ppm preferably 10 to 500 mole ppm in the treating gas. Furthermore, to facilitate temperature control of the chlorination treatment and to deposit the halogens more uniformly on the carrier, the treatment may be carried out in a fluidized bed of active alumina, although it can also be done in a fixed bed of active alumina.

The pressure for the chlorination treatment is not particularly restricted. It is desirable however to avoid pressures at which chlorine or its compounds might condense on the catalyst, and therefore pressures near atmospheric pressure are preferred. The chlorine compound referred to hereunder includes carbon tetrachloride, chloroform, dichloro-methane, ethyl chloride, isopropyl chloride, t-butyl chloride, trichloro-ethylene, hydrogen chloride and other chlorine-containing compounds.

Reactions or re-activation when repeated would result in progressive loss of fluorine in the catalyst. As fluorine diminishes to a point less than 70% of a fresh catalyst, the yield of isobutylene begins to decline. If this happened upon completion of the calcination treatment of the catalyst, both fluorine and chlorine should be supplied as already stated. Again, the term halogenation treatment according to the invention embraces both chlorination of the character above described and a similar process employing different halogen compounds. Such halogen compounds may be suitably selected depending upon the contents of fluorine and chlorine that exist after the calcination treatment of the used catalyst.

The proper amount of halogen to be replenished or added may be calculated from the formulae $$(A-A')wt\% \quad (1)$$

$$(B-B')wt\% \quad (2)$$

where A and B represent the rates of content of fluorine and chlorine respectively, in a fresh catalyst, and A' and B' represent the rates of content of fluorine and chlorine that exist upon calcination of the used catalyst. The optimum value of each of A and B varies with the alumina used and the particular halogenation conditions, but usually ranges from 0.6-2.0 wt% per catalyst weight for chlorine and from 0.3-1.0 wt% per catalyst weight for fluorine.

Halogen compounds contemplated hereunder may be mixtures of chlorine & fluorine, chlorine & a fluorine compound, a chlorine compound & fluorine, and a chlorine compound & a fluorine compound and further include other compounds containing in the molecule both chlorine and fluorine.

The fluorine compound referred to herein includes carbon tetrafluoride, di ethyl fluoride, isopropyl fluoride, t-butyl fluoride, trichloro-ethylene and hydrogen fluoride.

The term compound containing in the molecule both chlorine and fluorine as used herein corresponds to what is commonly known as "frons" including $CHClF_2$, $CCl_2F_2$, $CClF_3$, $CHCl_2F$, $CCl_3F$, $CH_2ClF$, $CCl_2F-CCl_2F$, $CCl_2F-CCl_2$ and $CF_3-CClF_2$. These "frons" may be used singly or in combination, or may be admixed with carbon tetrachloride, chlorine, hydrogen chloride, fluorine, hydrogen fluoride and the like depending upon the amount required of halogen to be replenished.

Straight chain aliphatic olefins to be isomerized by the re-activated catalyst of this invention include an aliphatic olefin usually having 4 to 24 carbon atoms, preferably 4 to 6 carbon atoms. It may be a single compound or a mixture of two or more compounds, or may be further mixed with a saturated hydrocarbon. Preferably, prior to the isomerization reaction, acetylene or dienes in the starting material are removed completely or nearly completely by extraction or selective hydrogenation thereby ensuring prolonged activity of the catalyst. The catalyst obtained in accordance with this invention finds most effective application in isomerizing n-butene to isobutene, and may further be used to isomerize n-pentene to isopentene.

The isomerization reaction according to the invention may be effected with an aliphatic olefin alone or a hydrocarbon mixture containing the same with or without dilution with a diluting gas such as nitrogen, carbon dioxide, helium or hydrogen. The reaction is carried out at a temperature from 200° to 600° C., preferably from 350° to 550° C. Lower reaction temperatures would result in premature reaction, while higher temperatures would result in undesirable side reactions such as disproportionation, hydrogen transfer or decomposition.

The reaction pressure may usually be in the neighborhood of atmospheric pressure, or may be anywhere as long as the reactant gases are maintained in gaseous phase. The rate of feeding the starting material, in terms of the gas hourly space velocity (GHSV), is 100 to 10,000 V/V/hr, preferably 300 to 3,000 V/V/hr, based on the aliphatic olefin. Selectivity of the isomerization reaction may be enhanced by retaining a small amount of moisture in the reaction system.

In the isomerization of olefins using the re-activated catalyst, the catalyst may be used as a fixed bed or fluidized bed. A gaseous-phase reaction is however preferred.

The re-activated catalyst according to the invention finds another useful application in oligomerization of olefins usually including aliphatic olefins of $C_2-C_{12}$, preferably $C_2-C_8$ which may be used alone or in combination, or may be of a straight chain or a branched chain or both. These olefins may be typically propylene, n-butene, isobutene, n-pentene and isopentene. The oligomerization reaction is effected at a temperature of from 30° to 350° C., preferably from 100° to 250° C., and at a pressure from atmospheric to 150 kg/cm²G, preferably from 15 kg/cm²G to 80 kg/cm²G. The feed is rated at 0.1 to 20, preferably 0.1 to 10 by liquid hourly space velocity (LHSV).

The re-activated catalyst of the invention finds a further application in converting methanol into hydrocarbons, particularly into olefins. This reaction is effected at a temperature of from 250° to 600° C., preferably from 300° to 500° C., at a pressure from atmospheric to 50 kg/cm²G and a feed rate of from 0.1 to 20 LHSV.

The catalyst of the invention finds still another application in isomerization, disproportionation and transalkylation of aromatic hydrocarbons including preferably alkylbenzenes of $C_7-C_{10}$. These reactions may be carried out at a temperature of from 200° to 700° C., preferably from 300° to 600° C., at a pressure of from atmospheric to 100 kg/cm²G, preferably from atmospheric to 50 kg/cm²G, and at a feed rate of from 0.1 to 20 LHSV, preferably from 1 to 5 LHSV. The reactions may be effected in the presence of hydrogen gas which serves to suppress accumulation of carbons on the catalyst and thus to prolong the catalyst life. The amount of this hydrogen is usually from equi-mole to 20 times greater by mole, preferably from equi-mole to 10 times greater by mole than the reactant aromatic hydrocarbon.

The invention will be further described by way of the following examples which are only illustrative but not limiting.

EXAMPLE I

Commercially available Ketjen B type alumina (tradename of Akzo Chemie; X-ray diffraction analysis: boehmite, $Na_2O$ 0.07 wt%, $SO_4$ 0.8 wt%, $SiO_2$ 0.9 wt%, Fe 0.03 wt%, surface area 340 m²/g) was compression-molded into tablets each having a size of 2 mm $\phi \times 2$ mm. The tablets were pulverized at a size of 20 to 30 mesh and calcined in an air atmosphere at 500° C. for 4 hours. After cooling, the calcined product was taken out and disposed in the air for 100 hours. The product showed a weight increase of 10.8 wt%. It was further calcined in an air atmosphere again at 500° C. for 4 hours to remove moisture that had been absorbed. The thus calcined product was again disposed in the air to absorb environmental moisture. The resulting alumina showed a weight increase of 10.4% as compared to its weight measured at the time of the second calcination. After being exposed to the air, 11 grams of the alumina was taken into a quartz reaction tube and dried at 500° C. for 1.5 hours with nitrogen fed at a rate of 250 ml/min. Halogenation was effected by passing 2.5 ml/min. of $CCl_2F_2$ gas and 250 m/min. of nitrogen containing 20 ppm of moisture through the tube over 20 minutes. The halogenated product contained 0.70% by weight of fluorine and 1.18% of chlorine. For purposes of illustration, this product is herein referred to as Catalyst A-1.

Isomerization of 1-butene was carried out with use of Catalyst A-1, in which a starting material was 1-butene of 98.1 mole purity (containing 1.5 mole % of n-butane) diluted two times with nitrogen, and the starting material was reacted at 400° C., at atmospheric and at 1,000 GHSV. The composition of the gas at the outlet of the tube was analyzed upon a lapse of 5 hours to show 4.3 wt% of $<C_4$, 60.2 wt% of n-butene, 30.9 wt% of i-butene, 0.8 wt% of n-butene and 3.8 wt% of $>C_4$. The outlet gas was further analyzed 50 hours after initiation of the reaction, whereupon its composition contained 2.0 wt% of $<C_4$, 68.5 wt% of n-butene, 27.5 wt% of i-butene, 0.9 wt% of n-butane and 1.1 wt% of $>C_4$, indicating a noticeable decline in the catalyst activity. At this point, the starting gas was discontinued and the tube temperature was lowered to 300° C. by passage of nitrogen. Thereafter, nitrogen containing 2% of oxygen was introduced to elevate the temperature slowly up to 500° C. with 1,000 GHSV thereby burning heavier hydrocarbons off the catalyst. This was done until carbon dioxide was barely present at the tube outlet. Here, the catalyst contained 0.67 wt% of fluorine and 0.74 wt% of chlorine. The reaction temperature was reduced to 340° C., followed by replacement of the reactant fluid with nitrogen containing 200 ppm of moisture. Part of this nitrogen was passed through carbon tetrachloride of 0° C. to be entrained therewith and brought into contact with the catalyst for 5 minutes, whereupon the temperature of the catalyst layer increased to 350° C. The catalyst thus treated contained 1.24 wt% of chlorine and is for purposes of illustration referred to herein as Catalyst A-2. This re-activated catalyst was used for isomerization under conditions similar to those in the case of A-1 above. After 5 hours of reaction, the outlet gas was analyzed to show 4.0 wt% of $<C_4$, 59.6 wt% of n-butene, 31.3 wt% of i-butene, 1.1 wt% of n-butane and 4.0 wt% of $>C_4$, this composition being well comparative with that obtained with Catalyst A-1.

EXAMPLE II

Dispural (trademark, beomite $\alpha$-AlOOH) available from Condea Inc. was added with 20 wt% of water and kneaded and thereafter extrusion-molded to a particle size of 1.5 mm in diameter. The molded material was dried in the air over a full day and further dried at 150° C. over another day. The dried material was taken into an electric furnace and calcined at 500° C. for 4 hours in the presence of air current. The same was cooled and thereafter exposed to the atmosphere for two consecutive days, whereupon it showed a weight increase of 10%. The material was again put into the furnace and calcined at 500° C. for 4 hours. After being cooled, the calcined material was disposed in the air for two consecutive days. This is for purposes of illustration referred to herein as Alumina I which had a water content of about 8 wt%. Alumina I was pulverized to a mesh size of 30-60, and 35 grams of this was taken into a pyrex halogenator measuring 35 mm $\phi \times 300$ mm, to the bottom of which nitrogen containing 200 ppm of water was introduced at a rate of 240 l/hr. to fluidize the alumina. The treatment temperature was raised to 340° C., whereupon gaseous Freon-12 ($CCl_2F_2$) was added at a rate of 6.3 ml/min. to be entrained with nitrogen and continued to pass at 350° C. for 24 minutes. The resulting halogenated catalyst contained 1.12 wt% of chlorine and 0.58 wt% of fluorine and is for purposes of illustration referred to herein as Catalyst B-1. This catalyst was used in skeleton isomerization of 1-butene, in which the starting material was 1-butene of 98.1 vol.% purity. This was equivalently diluted with nitrogen. The reaction temperature was 400° C., GHSV (1-butene) was 1,000 and the reaction pressure was atmospheric. The resulting gas composition at the reactor outlet is tabulated below.

TABLE 1

| | Reactor Outlet Gas Composition | | |
|---|---|---|---|
| | After 5 hrs. of Reaction | After 30 hrs. of Reaction | After 50 hrs. of Reaction |
| $C_4$ | 5.2 | 2.0 | 1.6 |
| $C_4$s | 1.5 | 0.5 | 0.2 |
| n-$C_4$s | 51.6 | 64.2 | 67.9 |
| i-$C_4$ | 36.0 | 31.2 | 29.8 |
| $>C_4$ | 5.7 | 2.1 | 0.5 |

After 50 hours of reaction, the catalyst activity declined sharply as compared to that noted initially. Therefore, the procedure of Example I was followed in the removal of high molecular weight hydrocarbons and in the supply of chlorine with carbon tetrachloride. This re-activated catalyst is referred to herein as Catalyst B-2. Halogen analysis was made as shown in Table 2 below.

TABLE 2

|  | Fresh Catalyst | Halogen in Catalyst After 50 hrs. of Reaction | After Catalyst Burned | After Treated with CCl₄ |
|---|---|---|---|---|
| Chlorine (wt %) | 1.12 | 0.87 | 0.67 | 1.16 |
| Fluorine (wt %) | 0.58 | 0.57 | 0.55 | 0.55 |

The reaction was effected with Catalyst B-2 in the manner and conditions similar to Example I, whereupon the outlet gas after 5 hours of reaction was analyzed to contain 5.6 wt% of $<C_4$, 1.6 wt% of $C_4$s, 50.8 wt% of n-$C_4'$, 36.2 at % of i-$C_4'$ and 6.8 wt% of $>C_4$.

EXAMPLE III

Catalyst B-2 after 50 hours of use (with replenishment of halogen for the amount used in analysis) was subjected to calcination and halogenation treatments in the manner described in Example I. The procedure of Example I was also followed in effecting the reaction for 50 hours and repeating the same reaction 10 times, whereupon the catalyst was calcined and thereafter analyzed to contain 0.65 wt% of chlorine and 0.39 wt% of fluorine. Activity of the catalyst after the last cycle of reaction declined considerably as compared to the fresh catalyst, as the outlet gas contained 30 wt% of i-$C_4'$. The used catalyst here is referred to herein as Catalyst C-1. 10 grams of this catalyst was taken into a fluidized bed halogenator, to the bottom of which nitrogen containing 200 ppm of moisture was introduced to fluidize the catalyst. The reactor temperature was raised to 340° C., whereupon gaseous Freon-11 ($CCl_3F$) was passed at a rate of 5.9 ml/min. to be entrained with nitrogen. This treatment was continued for 12 minutes. The temperature increased to 350° C. as halogen was entrained. The catalyst thus re-activated was analyzed to reveal 1.20 wt% of chlorine and 0.59 wt% of fluorine, and is for purposes of illustration referred to herein as Catalyst C-2. This catalyst was used for skeleton isomerization of 1-butene under the same conditions as in Example I. After 5 hours of reaction, the outlet gas composition was analyzed to show 4.7 wt% of $>C_4$, 1.3 wt% of $C_4$s, 52.5 wt% of n-$C_4'$, 36.5 wt% of i-$C_4'$ and 5.0 wt% of $>C_4$, indicating activity comparable to a fresh catalyst.

EXAMPLE IV

The procedure of Example II was followed in halogenating Alumina I except that Freon-12 treatment was continued for 50 minutes. The resulting catalyst contained 1.5 wt% of chlorine and 0.97 wt% of fluorine and is referred to herein as Catalyst D-1. This catalyst was used for oligomerization of isobutene, in which the starting material was isobutene of 99.2 wt% purity and 2 mole times greater toluene was used as solvent. The reaction was carried out at 120° C., at 50 kg/cm²G and at 1.0 LHSV. Isobutene was almost totally consumed after a lapse of 50 hours from the initiation of reaction. Thereafter, isobutene in the product was gradually increased. The product at the initial reaction stage contained tetramers, trimers and dimers in about 2.5 and 3 wt%, respectively. Tetramers and trimers diminished with time, while dimers increased. After a lapse of 58 hours, dimers were 80 wt%, trimers were 20 wt% and tetramers were only appreciable. Reaction was discontinued upon lapse of 55 hours. The catalyst was washed well with toluene, and toluene was thereafter purged with nitrogen. The reactor temperature was raised to 300° C., and air was introduced to maintain 2% oxygen. The temperature was increased slowly up to 500° C. at 1,000 GHSV. Heavier hydrocarbons were burned off the catalyst, until there was little or no carbon dioxide. The catalyst after being cooled contained 0.95 wt% of fluorine and 0.97 wt% of chlorine. This catalyst was treated with tetrachloride in the manner described in convertion with Example III. The catalyst thus treated contained 1.52 wt% of chlorine, and is referred to herein as Catalyst D-2. This catalyst was used for oligomerization of isobutene in the same condition as in the case of Catalyst D-1. Catalyst D-2 showed activity quite comparable to that of Catalyst D-1 over 50 hours following the initiation of reaction.

What is claimed is:

1. In the re-activation of a solid acid catalyst consisting essentially of an active alumina carrier and fluorine and chlorine both supported thereon, the amounts of said fluorine and said chlorine being 0.3–1.0% and 0.6–2.0%, respectively, based on the total weight of the catalyst composition, the process of re-activation which comprises:

(i) subjecting the catalyst to a calcination treatment at 350°–550° C. in which it is brought into contact with an inert gas containing less than 1 mole % of molecular oxygen thereby to burn off high molecular weight hydrocarbons that have been deposited on the catalyst during reaction;

(ii) measuring the contents of fluorine and chlorine in the calcined catalyst to see if the content of fluorine is greater or smaller than 70% of the fresh catalyst;

(iii) subjecting the calcined catalyst to a halogenation treatment at 200°–500° C. in which it is brought into contact with an inert gas or a non-reducing gas containing 50–1,000 ppm of moisture and entrained with chlorine, a chlorine compound or a mixture thereof, in the event the catalyst upon said calcination treatment contains fluorine in an amount greater than 70% of a fresh catalyst; and (iv) alternatively, subjecting the calcined catalyst to a halogenation treatment in which it is brought into contact with an inert gas or a non-reducing gas containing 50–1,000 ppm of moisture and entrained with a mixture of chlorine and fluorine, chlorine and a fluorine compound, a chlorine compound and fluorine, a chlorine compound and a fluorine compound, or a compound containing in the molecule both chlorine and fluorine, in the event the catalyst upon said calcination treatment contains fluorine in an amount less than 70% of a fresh catalyst.

2. The process according to claim 1, in which said chlorine compound is one selected from the group consisting of carbon tetrachloride, chloroform, dichloromethane, ethyl chloride, isopropyl chloride, t-butyl chloride, trichloro-ethylene, hydrogen chloride and other chlorine-containing compounds.

3. The process according to claim 1, in which said fluorine compound is one selected from the group consisting of carbon tetrafluoride, difluoro-methane, ethyl fluoride, isopropyl fluoride, t-butyl fluoride, trichloro-ethylene and hydrogen fluoride.

* * * * *